(12) United States Patent
Ehrenreich (10) Patent No.: US 9,149,265 B2
(45) Date of Patent: Oct. 6, 2015

(54) HINGED TISSUE SUPPORT DEVICE (75) Inventor: Kevin J. Ehrenreich, San Francisco, CA (US)

(73) Assignee: ABBOTT CARDIOVASCULAR SYSTEMS, INC., Santa Clara, CA (US)

( * ) Notice: Subject to any disclaimer, the term of this patent is extended or adjusted under 35 U.S.C. 154(b) by 306 days.

(21) Appl. No.: 13/035,939

(22) Filed: Feb. 26, 2011

(65) Prior Publication Data

US 2012/0220833 A1   Aug. 30, 2012

(51) Int. Cl.
*A61B 17/88* (2006.01)
*A61B 17/02* (2006.01)
*A61B 1/32* (2006.01)

(52) U.S. Cl.
CPC .. *A61B 17/02* (2013.01); *A61B 1/32* (2013.01)

(58) Field of Classification Search
CPC .......... A61B 17/7068; A61B 17/7067; A61B 17/7059; A61B 17/7062; A61B 17/7064
USPC ................ 606/246–249, 90, 105; 623/17.11; 600/219, 201–210
See application file for complete search history.

(56) References Cited

U.S. PATENT DOCUMENTS

| | | | |
|---|---|---|---|
| 2,238,563 A * | 4/1941 | Jacques | 27/21.1 |
| 2,416,260 A | 2/1947 | Karle | |
| 2,449,235 A | 9/1948 | Krupp | |
| 3,766,610 A | 10/1973 | Thorsbakken | |
| 3,877,434 A | 4/1975 | Ferguson et al. | |
| 4,156,574 A | 5/1979 | Boden | |
| 4,705,040 A | 11/1987 | Mueller et al. | |
| 4,750,492 A | 6/1988 | Jacobs | |
| 4,807,333 A | 2/1989 | Boden | |
| 5,292,332 A | 3/1994 | Lee | |
| 5,342,393 A | 8/1994 | Stack | |
| 5,364,408 A | 11/1994 | Gordon | |
| 5,383,905 A | 1/1995 | Golds et al. | |
| 5,391,200 A * | 2/1995 | KenKnight et al. | 607/129 |
| 5,417,699 A | 5/1995 | Klein et al. | |
| 5,435,044 A | 7/1995 | Ida | |
| 5,454,140 A | 10/1995 | Murai | |
| 5,462,558 A | 10/1995 | Kolesa et al. | |
| 5,478,353 A | 12/1995 | Yoon | |
| 5,501,692 A | 3/1996 | Riza | |
| 5,507,754 A | 4/1996 | Green et al. | |
| 5,520,070 A | 5/1996 | Beugelsdyk et al. | |
| 5,520,702 A | 5/1996 | Sauer et al. | |
| 5,562,688 A | 10/1996 | Riza | |
| 5,562,689 A | 10/1996 | Green et al. | |
| 5,569,306 A | 10/1996 | Thai | |
| 5,572,770 A | 11/1996 | Boden | |

(Continued)

FOREIGN PATENT DOCUMENTS

| | | |
|---|---|---|
| WO | WO 02/15795 | 2/2002 |
| WO | WO 2005/027754 | 3/2005 |

OTHER PUBLICATIONS

U.S. Appl. No. 13/022,246, Nov. 28, 2012, Office Action.

(Continued)

*Primary Examiner* — Mary Hoffman
*Assistant Examiner* — Tara R Carter
(74) *Attorney, Agent, or Firm* — Workman Nydegger; Randy Shen (57) ABSTRACT

A tissue support device is provided for managing access through tissue. The tissue support device engages the tissue proximate an opening in the tissue and biases the tissue support device to bring the engaged tissue together.

22 Claims, 4 Drawing Sheets

(56) References Cited

U.S. PATENT DOCUMENTS

| | | |
|---|---|---|
| 5,575,800 A | 11/1996 | Gordon |
| 5,613,974 A | 3/1997 | Andreas et al. |
| 5,630,824 A | 5/1997 | Hart |
| 5,645,553 A | 7/1997 | Kolesa et al. |
| 5,658,313 A | 8/1997 | Thal |
| 5,662,664 A | 9/1997 | Gordon et al. |
| 5,700,272 A | 12/1997 | Gordon et al. |
| 5,702,397 A | 12/1997 | Goble et al. |
| 5,725,529 A | 3/1998 | Nicholson et al. |
| 5,779,707 A | 7/1998 | Bertholet et al. |
| 5,868,762 A | 2/1999 | Cragg et al. |
| 5,893,856 A | 4/1999 | Jacob et al. |
| 5,899,921 A | 5/1999 | Caspari et al. |
| 5,902,311 A | 5/1999 | Andreas et al. |
| 5,941,901 A | 8/1999 | Egan |
| 6,066,160 A | 5/2000 | Colvin et al. |
| 6,086,608 A | 7/2000 | Ek et al. |
| 6,099,547 A | 8/2000 | Gellman et al. |
| 6,136,010 A | 10/2000 | Modesitt et al. |
| 6,190,414 B1 * | 2/2001 | Young et al. ............ 623/17.15 |
| 6,200,329 B1 | 3/2001 | Fung et al. |
| 6,203,554 B1 | 3/2001 | Roberts |
| 6,206,895 B1 | 3/2001 | Levinson |
| 6,228,096 B1 | 5/2001 | Marchand |
| 6,231,592 B1 | 5/2001 | Bonutti et al. |
| 6,245,080 B1 | 6/2001 | Levinson |
| 6,277,140 B2 | 8/2001 | Ginn et al. |
| 6,398,796 B2 | 6/2002 | Levinson |
| 6,475,230 B1 | 11/2002 | Bonutti et al. |
| 6,712,837 B2 | 3/2004 | Akerfeldt et al. |
| 6,746,457 B2 | 6/2004 | Dana et al. |
| 6,786,915 B2 | 9/2004 | Akerfeldt et al. |
| 7,011,400 B2 | 3/2006 | Nakano |
| 7,033,370 B2 | 4/2006 | Gordon et al. |
| 7,060,077 B2 | 6/2006 | Gordon et al. |
| 7,147,646 B2 | 12/2006 | Dana et al. |
| 7,320,693 B2 | 1/2008 | Pollack et al. |
| 7,361,183 B2 | 4/2008 | Ginn |
| 7,390,328 B2 | 6/2008 | Modesitt |
| 7,435,251 B2 | 10/2008 | Green |
| 7,662,161 B2 | 2/2010 | Briganti et al. |
| 7,713,284 B2 | 5/2010 | Crofford |
| 7,842,051 B2 | 11/2010 | Dana et al. |
| 7,875,043 B1 | 1/2011 | Ashby et al. |
| 7,931,670 B2 | 4/2011 | Fiehler et al. |
| 7,947,062 B2 | 5/2011 | Chin et al. |
| 8,048,108 B2 | 11/2011 | Sibbitt, Jr. et al. |
| 8,100,923 B2 | 1/2012 | Paraschac et al. |
| 8,128,652 B2 | 3/2012 | Paprocki |
| 8,128,653 B2 | 3/2012 | McGuckin, Jr. et al. |
| 8,262,736 B2 * | 9/2012 | Michelson ............... 623/17.16 |
| 8,337,522 B2 | 12/2012 | Ditter |
| 8,480,691 B2 | 7/2013 | Dana et al. |
| 8,579,934 B2 | 11/2013 | Ginn |
| 8,647,364 B2 | 2/2014 | Fiehler et al. |
| 8,932,324 B2 | 1/2015 | Sibbitt, Jr. et al. |
| 8,932,327 B2 | 1/2015 | Kosa et al. |
| 8,945,180 B2 | 2/2015 | Roorda |
| 2001/0023352 A1 | 9/2001 | Gordon et al. |
| 2001/0044638 A1 | 11/2001 | Levinson et al. |
| 2001/0044639 A1 | 11/2001 | Levinson |
| 2002/0002401 A1 | 1/2002 | McGuckin, Jr. et al. |
| 2002/0077658 A1 | 6/2002 | Ginn |
| 2002/0082641 A1 | 6/2002 | Ginn et al. |
| 2002/0107542 A1 | 8/2002 | Kanner et al. |
| 2002/0151921 A1 | 10/2002 | Kanner et al. |
| 2002/0169478 A1 | 11/2002 | Schwartz et al. |
| 2002/0188318 A1 | 12/2002 | Carley et al. |
| 2003/0093096 A1 | 5/2003 | McGuckin, Jr. et al. |
| 2003/0144695 A1 | 7/2003 | McGuckin, Jr. et al. |
| 2003/0167062 A1 | 9/2003 | Gamabale et al. |
| 2003/0195514 A1 * | 10/2003 | Trieu et al. ..................... 606/61 |
| 2003/0199987 A1 | 10/2003 | Berg et al. |
| 2004/0093024 A1 | 5/2004 | Lousararian et al. |
| 2004/0122451 A1 | 6/2004 | Wood |
| 2004/0158309 A1 | 8/2004 | Wachter et al. |
| 2005/0038500 A1 | 2/2005 | Boylan et al. |
| 2005/0085853 A1 | 4/2005 | Forsberg et al. |
| 2005/0096697 A1 | 5/2005 | Forsberg et al. |
| 2005/0205640 A1 | 9/2005 | Milliman |
| 2006/0190037 A1 | 8/2006 | Ginn et al. |
| 2006/0235505 A1 | 10/2006 | Oepen et al. |
| 2006/0241579 A1 | 10/2006 | Kawaura et al. |
| 2006/0265008 A1 | 11/2006 | Maruyama et al. |
| 2006/0265010 A1 | 11/2006 | Paraschac et al. |
| 2007/0010853 A1 | 1/2007 | Ginn et al. |
| 2007/0060895 A1 | 3/2007 | Sibbitt, Jr. et al. |
| 2007/0149987 A1 | 6/2007 | Wellman et al. |
| 2007/0255317 A1 | 11/2007 | Fanton et al. |
| 2007/0260125 A1 * | 11/2007 | Strauss et al. ............ 600/219 |
| 2007/0270904 A1 | 11/2007 | Ginn |
| 2007/0276433 A1 | 11/2007 | Huss |
| 2007/0276488 A1 | 11/2007 | Wachter et al. |
| 2008/0065156 A1 | 3/2008 | Hauser et al. |
| 2008/0114395 A1 | 5/2008 | Mathisen et al. |
| 2008/0312740 A1 | 12/2008 | Wachter et al. |
| 2009/0012537 A1 | 1/2009 | Green |
| 2009/0069847 A1 | 3/2009 | Hashiba et al. |
| 2009/0157102 A1 | 6/2009 | Reynolds et al. |
| 2009/0306671 A1 * | 12/2009 | McCormack et al. ......... 606/90 |
| 2009/0306685 A1 | 12/2009 | Fill |
| 2010/0042144 A1 | 2/2010 | Bennett |
| 2010/0179589 A1 | 7/2010 | Roorda et al. |
| 2010/0179590 A1 | 7/2010 | Fortson et al. |
| 2010/0256670 A1 | 10/2010 | Ginn et al. |
| 2011/0029012 A1 | 2/2011 | Tegels |
| 2012/0184991 A1 | 7/2012 | Paraschac et al. |
| 2013/0046331 A1 | 2/2013 | Christensen et al. |
| 2013/0103077 A1 | 4/2013 | Ditter |
| 2013/0110165 A1 | 5/2013 | Burkhart et al. |
| 2013/0218206 A1 | 8/2013 | Gadlage |
| 2013/0296887 A1 | 11/2013 | Dana et al. |
| 2013/0345745 A1 | 12/2013 | Kim |
| 2014/0148824 A1 | 5/2014 | Fujisaki et al. |
| 2014/0228868 A1 | 8/2014 | Hassan et al. |
| 2014/0336702 A1 | 11/2014 | Rowe et al. |
| 2014/0364904 A1 | 12/2014 | Kim |

OTHER PUBLICATIONS

U.S. Appl. No. 13/219,004, Dec. 19, 2012, Restriction Requirement.
U.S. Appl. No. 12/917,195, Jun. 28, 2012, Office Action.
U.S. Appl. No. 13/022,246, May 11, 2012, Office Action.
U.S. Appl. No. 12/917,195, Aug. 1, 2012, Office Action.
U.S. Appl. No. 13/411,320, filed Mar. 2, 2012, Voss et al.
U.S. Appl. No. 12/684,470, filed Jan. 8, 2010, Voss et al.
U.S. Appl. No. 12/917,195, filed Nov. 1, 2010, Voss et al.
U.S. Appl. No. 13/022,246, filed Feb. 7, 2011, Yribarren.
U.S. Appl. No. 13/219,004, filed Aug. 26, 2011, Roorda.
U.S. Appl. No. 12/917,195, May 6, 2013, Office Action.
U.S. Appl. No. 13/022,246, Jun. 7, 2013, Office Action.
U.S. Appl. No. 60/502,925, filed Sep. 15, 2003, Paraschac.
U.S. Appl. No. 10/941,693, Nov. 17, 2006, Office Action.
U.S. Appl. No. 10/941,693, May 7, 2007, Office Action.
U.S. Appl. No. 10/941,693, Dec. 31, 2007, Office Action.
U.S. Appl. No. 10/941,693, Jul. 9, 2008, Office Action.
U.S. Appl. No. 10/941,693, Mar. 2, 2009, Office Action.
U.S. Appl. No. 10/941,693, Oct. 23, 2009, Office Action.
U.S. Appl. No. 10/941,693, Sep. 28, 2011, Notice of Allowance.
U.S. Appl. No. 11/460,863, Jul. 12, 2007, Office Action.
U.S. Appl. No. 11/460,863, Feb. 5, 2008, Office Action.
U.S. Appl. No. 11/460,863, Oct. 10, 2008, Office Action.
U.S. Appl. No. 11/460,863, Apr. 13, 2009, Office Action.
U.S. Appl. No. 13/219,004, Feb. 14, 2013, Office Action.
U.S. Appl. No. 12/917,195, Aug. 7, 2013, Notice of Allowance.
U.S. Appl. No. 13/219,004, Aug. 9, 2013, Office Action.
U.S. Appl. No. 14/052,658, filed Oct. 11, 2013, Ehrenreich.
U.S. Appl. No. 12/917,195, Nov. 20, 2013, Issue Notification.
U.S. Appl. No. 13/022,246, Nov. 14, 2013, Notice of Allowance.
U.S. Appl. No. 13/356,129, May 6, 2014, Office Action.
U.S. Appl. No. 13/219,004, Aug. 5, 2014, Office Action.

(56) References Cited

OTHER PUBLICATIONS

U.S. Appl. No. 13/356,129, Sep. 15, 2014, Office Action.
U.S. Appl. No. 14/052,658, Sep. 4, 2014, Office Action.
U.S. Appl. No. 13/411,320, May 27, 2015, Notice of Allowance.
U.S. Appl. No. 13/219,004, May 27, 2015, Issue Notification.
U.S. Appl. No. 13/356,129, Mar. 18, 2015, Office Action.
U.S. Appl. No. 14/052,658, Mar. 27, 2015, Office Action.
Beartrap definition; http://en.wktionary.org/wiki/beartrap; 1 pg.; accessed Dec. 4, 2014.
U.S. Appl. No. 13/411,320, Feb. 3, 2015, Office Action.
U.S. Appl. No. 13/219,004, Feb. 17, 2015, Notice of Allowance.

* cited by examiner

HINGED TISSUE SUPPORT DEVICE

BACKGROUND

1. The Field of the Invention

Embodiments of the invention relate generally to medical devices. More particularly, embodiments of the invention relate to medical devices for managing access in body tissue including closing large holes in the body tissue.

2. The Relevant Technology

Catheterization and interventional procedures, such as angioplasty or stenting, are generally performed by inserting a hollow needle through a patient's skin and tissue into the patient's vascular system. A guide wire may be advanced through the needle and into the patient's blood vessel accessed by the needle. The needle is then removed leaving the guide wire in place, enabling an introducer sheath to be advanced over the guide wire into the vessel.

A catheter or other device may then be advanced through a lumen of the introducer sheath and over the guide wire into a position for performing a medical procedure. As the various devices are introduced through the introducer sheath, the opening or access site formed in the vessel may be subjected to additional trauma or tearing during the medical procedure.

Upon completing the procedure, the devices and introducer sheath are removed from the opening, leaving a puncture site or opening in the vessel wall. Traditionally, external pressure would be applied to the puncture site until clotting and wound sealing occur; however, the patient must remain bedridden for a substantial period after clotting to ensure closure of the wound. This procedure, however, may be time consuming and expensive, requiring as much as an hour of a physician's or nurse's time. It is also uncomfortable for the patient and requires that the patient remain immobilized in the operating room, catheter lab, or holding area. In addition, the insertion and removal of various medical devices can lead to problems such as enlarging or tearing the puncture, which can make it more difficult to close the opening.

BRIEF SUMMARY

Embodiments of the invention relate to a tissue support device. The tissue support device engages tissue proximate an opening in the tissue. The tissue support device is biased such that the tissue engaged by the tissue support device can be brought in proximity for closing.

In one example, the tissue support device manages access to an opening in tissue. The tissue support device includes first and second portions having corresponding engagement mechanisms. The engagement mechanisms are configured to engage the tissue proximate the opening. A biasing mechanism connects the first and second portions and biases the first and second portions to a closed position.

In another example, the tissue support device is configured to assist in closing an opening in tissue and/or manage access to a body lumen through the opening. The tissue support device includes first and second portions. Each of the first and second portions have a central regions extending between ends of the portions. An engagement mechanism extends laterally from each of the portions. The tissue support device also includes a biasing mechanism that joins the portions together. The biasing mechanism exerts a force to bias the portions to a closed position.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which at least some of the advantages and features of the invention can be obtained, a more particular description of the invention briefly described above will be rendered by reference to specific embodiments thereof, which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF EMBODIMENTS OF THE INVENTION

In general, embodiments of the invention relate to methods and devices for managing access to body lumens, for example by providing tissue support. Although various embodiments of the invention may be discussed with reference to a vessel, one of skill in the art can appreciate, with the benefit of the present disclosure, that embodiments of the invention can also be used in conjunction with other tissue, lumens, and/or with other procedures. Embodiments of the invention relate to a tissue support device for closing or managing holes including large holes in tissue. More specifically, embodiments of the invention relate to a tissue support device that manages access to tissue and that aids in closing openings formed to access the tissue.

In many medical procedures, it is often necessary to create an opening or an access site in tissue for various reasons, including to introduce medical devices into the tissue or into body lumens. For example, an opening (e.g., an arteriotomy) is often formed in a vessel during a stenting procedure. After the opening is formed in the vessel, other medical devices are often introduced into the vessel lumen through the same opening. These medical devices are often larger than the needle that originally formed the opening. As a result, the opening is likely to be enlarged in order to accommodate those medical devices. In other words, the insertion, use, and/or removal of these medical devices may cause additional trauma to the vessel (e.g., tearing of the vessel).

The opening in the vessel may also be due to trauma unrelated to a medical procedure, for example a wound or an accident. The size of the opening in the tissue may be relatively larger than, for example, an arteriotomy.

Embodiments of the invention relate to a tissue support device that may be placed around or proximate the opening formed in the vessel during these types of procedures or occurrences. The tissue support device may be configured to reduce or minimize trauma to the vessel as well as aid in closing the opening regardless of how the opening is formed (e.g., surgery, accident, wound, etc.). Embodiments of the invention are further configured for aiding in the closure of large holes, for example, when the vessel is almost completely open, or for bringing the walls of the vessel together such that the opening can be closed using a clip or sutures.

Embodiments of the invention may reduce or minimize tearing that may occur at the opening during the insertion, use, and/or removal of medical devices such as an introducer sheath or catheter or for other reasons. Minimizing or reducing trauma to the vessel, by way of example only, can improve recovery time, keep the size of the opening to a minimum, and/or make the procedure easier to perform.

Generally, the tissue support device is placed and/or anchored at a procedure site. The tissue support device, for example, may be placed in the tissue proximate the opening in the tissue. The tissue support device may be anchored at different locations around the opening. Anchoring the tissue support device in the tissue proximate the opening enables the tissue support device to control the size of the opening. When the tissue support device closes, for instance, the edges of the vessel defining the opening are brought closer together. Closure of the opening can then be completed, by way of example only, using other devices such as clips or sutures. Embodiments of the invention can therefore aid in closing openings formed in a vessel. The completion of the closure process may be achieved using other devices such as clips or sutures.

The tissue support device typically engages at least some of the tissue surrounding or proximate the opening in the tissue. Often, the tissue support device engages the tissue in various locations proximate the opening.

In order to close the opening and/or perform a procedure through the opening in the tissue, the tissue support device is configured to open and close. The tissue support device typically includes a biasing mechanism that urges the tissue support device to a closed position. While the tissue support device can be held in an open position (for example by the insertion of an apparatus through the tissue support device), the biasing mechanism closes the tissue support device when the apparatus is removed.

When a medical device needs to be introduced through the opening in the vessel, the tissue support device can be opened to allow entry of the medical device. Thus, the medical device is inserted through both the interior of the tissue support device and the opening in the tissue in order to be introduced into the body lumen. Often, the medical device itself operates to open the tissue support device to permit entry of the medical device into the opening in the vessel. Although the biasing mechanism biases the tissue support device to a closed position, the tissue support device does not typically interfere with the insertion, removal, and/or use of the medical device. The tissue support device may remain engaged with the tissue during the use of a medical device.

When the medical device is removed, the tissue support device may return to a closed position. In some examples, closing of the tissue support device may at least partially close the opening in the vessel. The tissue support device, in this sense, can therefore provide tissue support and provide pre-closure support as well.

The tissue support device includes engagement mechanisms that can engage the vessel wall (or other tissue) proximate the opening. The engagement mechanisms attach the tissue support device to the vessel wall. The engagement mechanisms, for instance, may pierce or at least partially pierce the tissue proximate the opening to anchor the tissue support device to the tissue. The engagement mechanisms remain attached to the tissue (or vessel wall) during opening and/or closing of the tissue support device.

When a medical device (e.g., an introducer sheath or catheter) needs to be introduced, the tissue support device is opened to enable introduction of the medical device via the opening through the tissue support device. When the medical device is withdrawn from the opening, the biasing mechanism of the tissue support device returns the tissue support device to its original position, closing or at least partially closing the opening in the vessel in some examples. In some instances, closure of the tissue support device brings the edges of the vessel defining the opening in proximity such that another device (e.g, a clip or sutures) can be used to complete the closure procedure.

Figure 1:
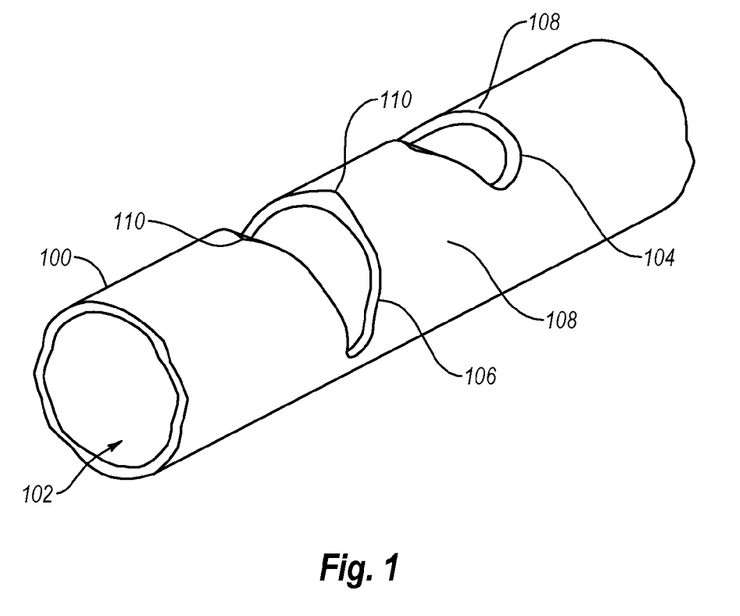
FIG. 1 is a perspective view of a vessel and illustrates an opening in the vessel as well as a large opening in the vessel.

FIG. 1 shows an example of a vessel 100. The vessel 100 shows openings 104 and 106. The opening 104 is an example of an opening (e.g., an arteriotomy) formed during a medical procedure and provides an access site for the medical procedure. The opening 106 is comparatively larger than the opening 104 and may also have been formed during a procedure, although the opening 106 may also be the result of a wound or accident.

Embodiments of the tissue support device disclosed herein can be used with large holes, such as the opening 106, as well as smaller holes, such as the opening 104. In this example, walls 108 are examples of tissue proximate the opening 104 and walls 110 are examples of tissue proximate the hole opening.

Figure 2:
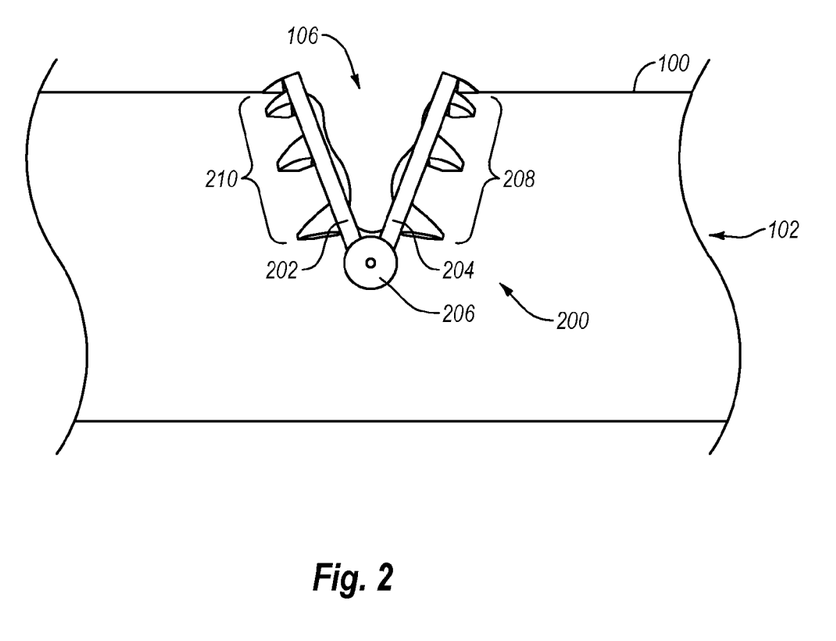
FIG. 2 illustrates a side view of a tissue support device for closing an opening in the vessel or for assisting in closing the opening.

FIG. 2 illustrates a side view of a tissue support device 200 for closing an opening in the vessel or for aiding in closing the opening in the vessel. The tissue support device 200 can provide tissue support, for example during a medical procedure.

The tissue support device 200 is positioned on the vessel 100 proximate the opening 106. The tissue support device 200 is configured to open and close and is typically biased towards a closed position.

The tissue support device 200 includes a portion 202, a portion 204 that are connected or joined by a biasing mechanism 206. The biasing mechanism 206 may be integral to either or both of the portions 202 and 204. Alternatively, the biasing mechanism 206 may be a separate component that is connected with the portions 202 and 204. The biasing mechanism 206 enables each of the portions 202 and 204 to rotate about an axis defined by the biasing mechanism 206 in one example. Typically, the tissue support device includes a pair of biasing mechanisms. The portions 202 and 204 are joined at the respective ends by the biasing mechanisms.

The portion 202 includes an engagement mechanism 210 and the portion 204 includes an engagement mechanism 208. The engagement mechanisms 208 and 210 can be configured to engage with the walls of the vessel 100 or other tissue. The engagement mechanisms 208 and 210 may engage with tissue that is proximate the opening 106. As a result, the tissue support device 200 can bring the edges of the opening 106 together during closure of the opening.

In the closed position, the portions 202 and 204 have substantially the same shape and may be in contact along their length or slightly separated in the closed position. Alternatively, the portions 202 and 204 may be shaped such that the portions 202 and 204 are only in contact in specific locations in the closed position.

The engagement mechanisms 208 and 210 may be integral with the portions 202 and 204. In addition, the engagement mechanisms 208 and 210 may extend from the portions 202 and 204 in order to engage with the tissue. The engagement mechanisms 202 and 204 can vary in terms of dimensions and configurations.

During deployment of the tissue support device 200, in one example, the tissue support device 200 is deployed in the closed position. The tissue support device 200 is then opened. The tissue support device 200 can open, for example, as the portions 202 and 204 rotate about an axis defined by the biasing mechanism 206. The tissue support device 200 can open, by way of example at least 180 degrees or more if necessary to engage the tissue.

Opening the tissue support device 200 causes the engagement mechanisms 208 and 210 to engage the tissue proximate the opening 106. Once the engagement mechanisms 208 and 210 engage the tissue, the tissue support device 200 brings the edges of the opening 106 together upon closing.

Figure 3:
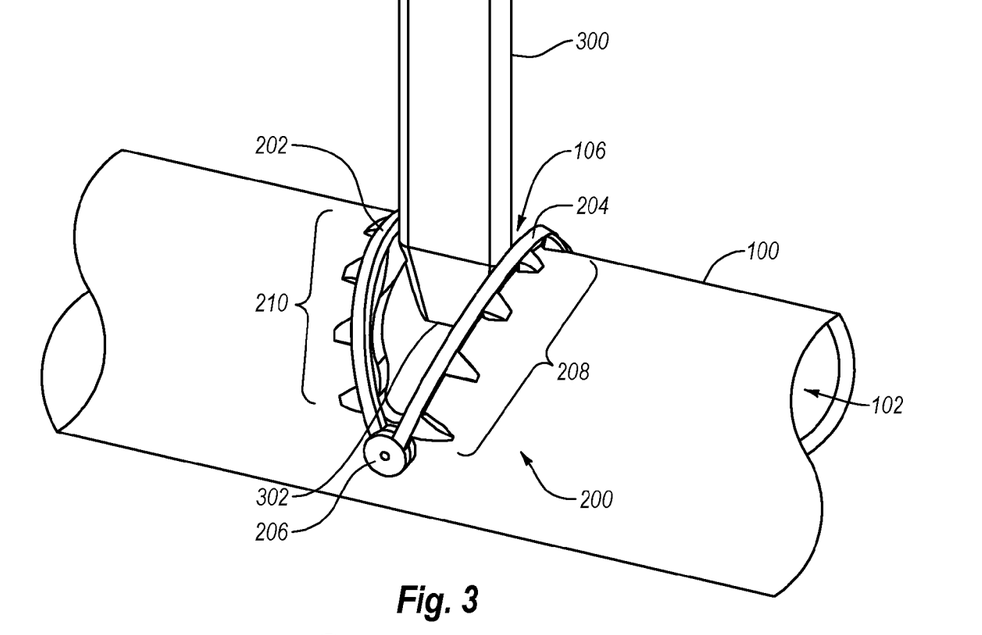
FIG. 3 illustrates an example of a device configured for opening a tissue support device.

FIG. 3 illustrates an example of a device configured for opening the tissue support device 200. In FIG. 3, a device 300 is inserted between the portions 202 and 204 to open the tissue support device 200. By way of example only, the device 300 may be an introducer sheath, a catheter, a needle, or other device. In one example, the device may have an end 302 that forms an edge or blade. The end 302 of the device may be configured to be inserted between the portions 202 and 204. As the end 302 is inserted further into the tissue support device 200, the device 300 may be configured to expand or open the tissue support device 200. In one example, the device 300 may be rotated to further open the tissue support device 200 and separate the portions 202 and 204 such that the engagement mechanisms 208 and 210 engage the walls of the vessel 100 around the opening 106. More specifically, the device 300 may be rotated (e.g, approximately 90 degrees) to open the tissue support device 200 and separate the portions 202 and 204. The end 302 of the device 300 may be configured like a blade that is thin in a first direction and comparatively thick in another direction.

Opening the engagement mechanisms 208 and 210 may cause the engagement mechanisms 208 and 210 to engage or attach to the walls of the vessel 100. Once the tissue support device 200 is engaged with the vessel 100, the portions 202 and 204 (and the engagement mechanisms 208 and 210) bring the walls defining the opening in the vessel closer together when the tissue support device 200 closes.

In one example, the device 300 may include an introducer sheath, a needle, a catheter, or the like. In addition, the device 300 can be used to hold the tissue support device 200 open while a procedure is performed through the tissue support device 200 and the opening 106. For example, the device 300 may be an introducer sheath and other medical devices can be introduced into the vessel's lumen through the introducer sheath. In another example, the various devices used to perform a procedure can each be inserted individually. In this case, the various devices can each be used to open the tissue support device 200 as necessary.

To facilitate opening the tissue support device 200, at least the portions 202 and 204 or a part thereof may be coated to reduce friction between the portions 202 and 204 and the various medical devices used during the medical procedure.

The biasing mechanism 206 of the tissue support device 200 closes or at least partially closes the opening 106 each time a device is withdrawn. This may help reduce, for instance, blood loss.

Figure 4A:
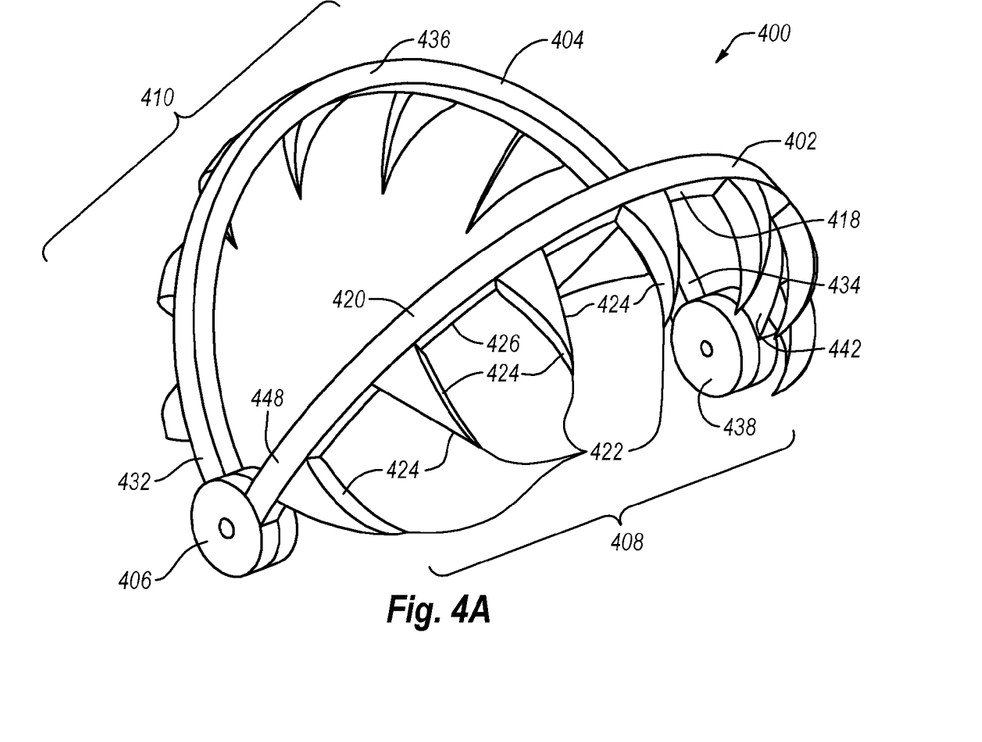
FIG. 4A shows an illustrative example of a tissue support device.

FIG. 4A shows an illustrative example of a tissue support device 400, which is an example of the tissue support device 200. The tissue support device 400 includes portions 402 and 404 that are joined by a biasing mechanism 406. In one example, the portions 402 and 404 and the engagement mechanism 406 may be a single integrated unit. Alternatively, the portions 402 and 404 may be joined by the biasing mechanism 406. Alternatively, one of the portions 402 and 404 may be integrally formed with the biasing mechanism 406.

FIG. 4A further illustrates that the portion 404 includes a central region 436 extending between an end 432 and an end 434. The end 432 is connected to or joins the biasing mechanism 406 while the end is connected to or joins the biasing mechanism 438. The portion 402 is similarly configured and includes ends 440 and 442 that are connected to or join with the biasing mechanisms 406 and 438, respectively. In this example, the portion 402 may be similarly configured like the portion 404.

The ends 432 and 434 and the central region 438 of the portion 404 have a generally arcuate shape. In other words, the portions 404 curves in a plane that includes the biasing mechanisms 406 and 438. In another example, the portion 404 may have a convex shape such that the portion 404 curves in at least two dimensions. When the portions 402 and 404 have a planar arcuate shape, the portions 402 and 404 may be in contact when the tissue support device 400 is in the closed position. When the portions 402 and 404 have a multidimensional curve, the portions 402 and 404 may not be in contact in the closed position.

FIG. 4A also illustrates engagement mechanisms 408 and 410, which are examples of the engagement mechanisms 208 and 210. The engagement mechanisms 408 and 410 includes needles 424. The needles 424 extend from a side 418 of the portion 402. Alternatively, the needles 410 may extend from a top 420 or bottom 426 of the portion 402.

In this example, the needles 424 are shaped to extend from the portion 402 and narrow to a point 422. The points 422 of the needles 424 can pierce (partially or completely) the walls of the vessel around the opening. The needles 424 can each be configured in a similar manner or in different manners. For instance, some of the needles may be shorter, thicker, have a different orientation, or the like or any combination thereof. More generally, the dimensions and/or orientations of the individual needles 424 can vary or be the same.

Figure 4B:
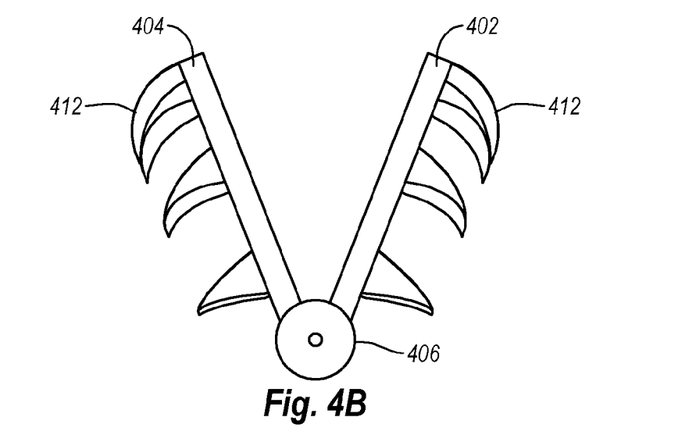
FIG. 4B shows an example of an engagement mechanism enabling the tissue support device to aid in closing the vessel.
Figure 4C:
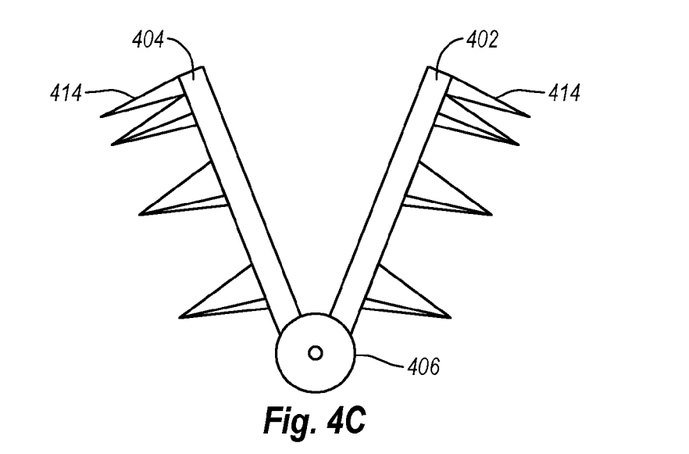
FIG. 4C shows another example of the engagement mechanism.
Figure 4D:
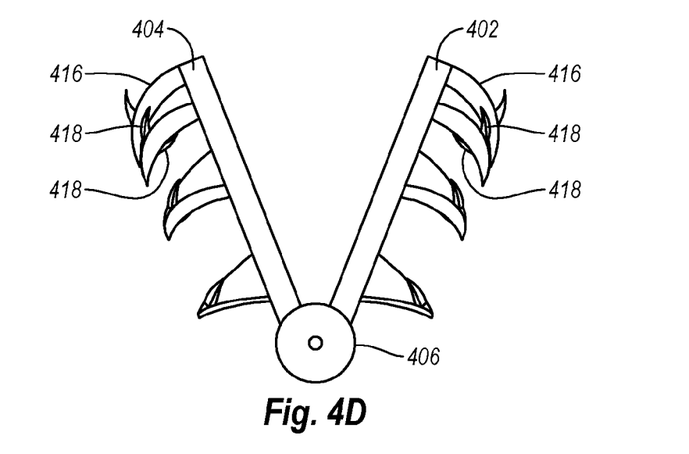
FIG. 4D shows another example of the engagement mechanism.

FIGS. 4B, 4C, and 4D illustrate examples of different configurations of the needles 424. FIG. 4B illustrates a needle 412 that curves inwardly as the needle extends from the portion 402. FIG. 4C illustrates needles 414 that extend out from the portion 402 substantially straight with little curve. FIG. 4D illustrates needles 416 that includes barbs 418. The barbs 418 on at least some of the needles 416 are typically configured to ensure that the needles 416 do not disengage from the vessel 100 after engaging with the vessel 100. The barbs 418 can be included on any of the various needles disclosed herein.

Figure 5:
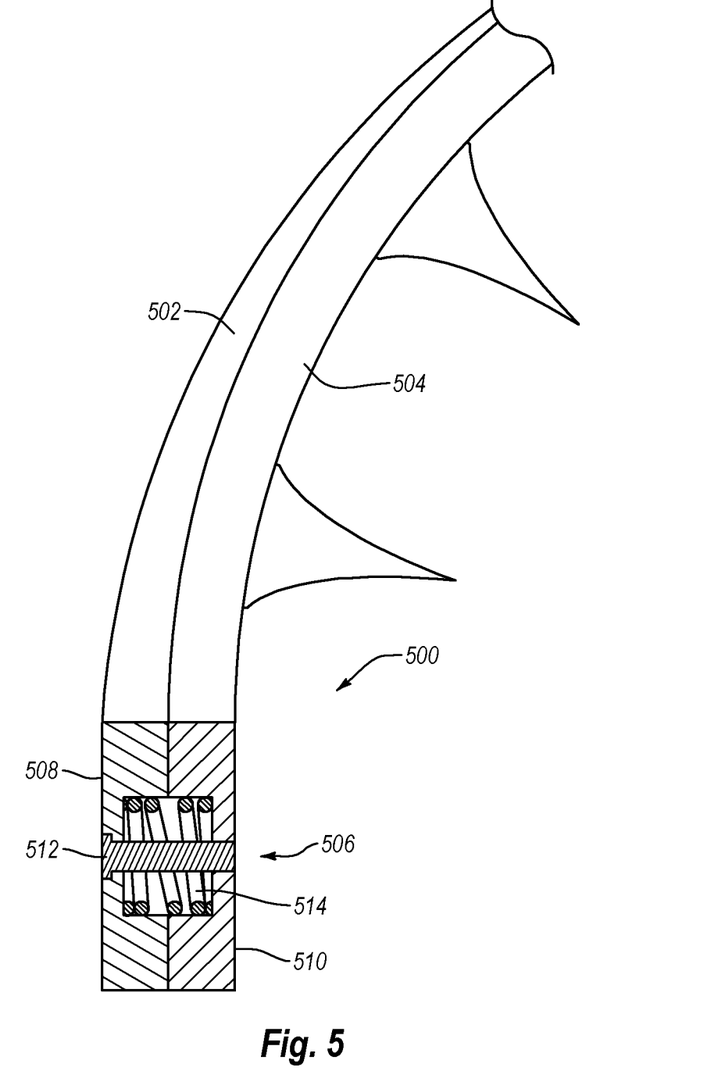
FIG. 5 shows an illustrative example of a biasing mechanism included in a tissue support device.

FIG. 5A illustrates an example of a biasing mechanism 506 in a tissue support device 500, which is an example of the tissue support device 200. The biasing mechanism 506 includes an end 508 and an end 510. The end 508 and the end 510 are joined at a pivot 512 that enables the ends 508 and 510 to rotate relative to each other. As the tissue support device 500 opens, the ends 508 rotate about the pivot 512. In another example, the pivot 512 may correspond to a portion of the tissue support device 500 that flexes when the portions 502 and 504 are separated. As the pivot 512 flexes, the pivot 512 exerts a force to bias the tissue support device to the closed position.

In this example, the ends 508 and 510 are at least partially hollow. A spring 514 is disposed inside of the ends 508 and 510 and arranged to pass through the pivot 512. The ends 508 and 510 typically include a stop disposed in their interiors against which the ends of the spring 514 rest. As the tissue support device opens, the stops (or more generally the portions 502 and 504) push against the ends of the spring 514. As the tissue support device 500 opens, the spring 514 exerts a force that biases the tissue support device 500 to the closed position. The spring 514 is typically strong enough to close the tissue support device 500 after the tissue support device 500 is engaged with the tissue.

In another example, the bias mechanism 506 includes a hinge and the portions 502 and 504 open and close about the hinge.

In another example, the bias mechanism 506 may include a shape memory material. In this case, the tissue support device 500 can be deformed when opening or when inserting a medical device. The bias mechanism returns to a set shape, for example, when the medical device is removed.

In one embodiment, the portions 502 and 504 may be relatively inflexible. In this example, the relative movement of the portions 502 and 504 is accomplished through the bias mechanism.

The tissue support device 500 is configured to close large holes, for example, when the vessel is almost completely open. The tissue support device 500 can be opened at least 180 degrees such that the tissue support device is relatively flat. This enables the tissue support device 500 to be used with large holes.

In one embodiment, the tissue support device can include a variety of suitable deformable alloy metal materials, including stainless steel, silver, platinum, tantalum, palladium, cobalt-chromium alloys or other known biocompatible alloy metal materials.

In one embodiment, the tissue support device may also include shape memory materials.

In one embodiment, the tissue support device can include a suitable biocompatible polymer in addition to or in place of a suitable metal. The tissue support device can include biodegradable or bioabsorbable materials, which may or may not be elastically deformable.

It is further contemplated that the external surface and/or internal surface of the tissue support device or tissue support device element (e.g., exterior and/or luminal surfaces) can be coated with another material having a composition different from a primary tissue support device material. The use of a different material to coat the surfaces can be beneficial for imparting additional properties to the tissue support device, such as providing radiopaque characteristics, drug-reservoirs, and improved biocompatibility.

In one configuration, the external and/or internal surfaces of the tissue support device can be coated with a biocompatible polymeric material as described herein. Such coatings can include hydrogels, hydrophilic and/or hydrophobic compounds, and polypeptides, proteins or amino acids or the like. Specific examples can include polyethylene glycols, polyvinylpyrrolidone (PVP), polyvinylalcohol (PVA), parylene, heparin, phosphorylcholine, polytetrafluoroethylene (PTFE), or the like.

Accordingly, the coating material can contain a drug or beneficial agent to improve the use of the tissue support device. Such drugs or beneficial agents can include antibiotics, for example.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A tissue support device for managing access to an opening in tissue, the tissue support device comprising:
a first curved portion having a first engagement mechanism configured to engage the tissue proximate the opening in the tissue, the first curved portion extending in an arc along a curved longitudinal axis from a first end to a second end, the first curved portion being elongate along the curved longitudinal axis from the first end to the second end;
a second curved portion having a second engagement mechanism configured to engage the tissue proximate the opening in the tissue, the second curved portion extending in an arc along a curved longitudinal axis from a first end to a second end, the second curved portion being elongate along the curved longitudinal axis from the first end and to the-second end; and
a biasing mechanism connecting the first curved portion and the second curved portion, the first curved portion and the second curved portion having an open position in which the first curved portion and the second curved portion form a closed, annular opening approximating the opening in the tissue and an outer circumferential surface of the tissue support device, the biasing mechanism including a first biasing mechanism connecting the first ends of the first curved portion and the second curved portion and a second biasing mechanism connecting the second ends of the first curved portion and the second curved portion,
wherein the first and second biasing mechanisms bias the first curved portion and the second curved portion towards a closed position such that the opening is reduced in size in the closed position,
wherein the biasing mechanism enables the first curved portion and the second curved portion to open at least 180 degrees while still approximating the opening in the tissue;
wherein the open position facilitates the biasing mechanism engaging the tissue proximate the opening and the closed position facilitates bringing edges of the tissue opening together to a proximity that allows closure of the opening by a clip or sutures.

2. The tissue support device of claim 1, wherein the first curved portion and the second curved portion curve in planes that intersect with the first and second biasing mechanisms, and wherein the first and second curved portions are configured to move between the closed position and the open position by rotating about an axis extending through the first and second biasing mechanisms.

3. The tissue support device of claim 1, wherein the first curved portion and the second curved portion are have a concave shape.

4. The tissue support device of claim 1, wherein the biasing mechanism includes a first hinge and a second hinge, wherein the first hinge joins first ends of the first and second curved portions and the second hinge joins the second ends of the first and second curved portions, and wherein the first and second hinges have cylindrical housings encasing the first and second ends of the first and second curved portions.

5. The tissue support device of claim 1, wherein the biasing mechanism comprises at least one spring, wherein the spring is positioned inside of the biasing mechanism.

6. The tissue support device of claim 1, wherein the first engagement mechanism and the second engagement mechanism each comprise a plurality of needles that extend laterally outward from, and that are spaced apart along the longitudinal axis of the first curved portion and the second curved portion.

7. The tissue support device of claim 6, wherein at least some of the needles comprise barbs that are angled to facilitate insertion of the plurality of needles into the tissue while resisting removal of the one or more needles from the tissue.

8. The tissue support device of claim 6, wherein the plurality of needles curve inwardly toward the opening in the tissue when engaged with the tissue.

9. The tissue support device of claim 6, wherein the plurality of needles include increasing curvature from the ends of the first and second members towards apexes of the first and second members, such that needles having little to no curvature are located at the ends of the first and second members and needles curving reflexively inward are located at apexes of the first and second members.

10. The tissue support device of claim 1, wherein the first biasing mechanism comprises a first pivot member that passes through first openings in the first ends of the first member and the second member, the first pivot member further including a first spring housed within a first portion of the first openings;
wherein the second biasing mechanism comprises a second pivot member that passes through second openings in the second ends of the first member and the second member, the second pivot member further including a second spring housed within a second portion of the second openings;
wherein the first ends of the first member and the second member rotate relative to the first pivot member and the second ends of the first member and the second member rotate relative to the second pivot member; and
wherein the first and second springs that are disposed within the first and second openings exert a force that biases the first member and the second member to the closed position.

11. The tissue support device in claim 1, wherein the first and second biasing mechanisms include smooth, circular medial and lateral facing surfaces.

12. The tissue support device in claim 1, wherein the first and second members include one or more convex shapes that provide one or more waves along lengthwise directions of the elongated members, such that the first and second curved portions have multidimensional curves.

13. A tissue support device for assisting in closing an opening in tissue, the tissue support device comprising:
a first curved portion extending in an arc along a curved longitudinal axis from a first end to a second end and having a first central region extending therebetween, the first curved portion being elongate along the curved longitudinal axis and having a first engagement mechanism extending laterally;
a second curved portion extending in an arc along a curved longitudinal axis from a first end to a second end and having a second central region extending therebetween, the second curved portion being elongate along the curved longitudinal axis and having a second engagement mechanism extending laterally in a direction substantially opposed to the first engagement mechanism when the first curved portion and the second curved portion are in a closed position;
a biasing mechanism joining the first end of the first curved portion with the first end of the second curved portion and joining the second end of the first curved portion with the second end of the second curved portion, such that the first curved portion and the second curved portion have an open position where the first portion and the second portion form a closed, annular opening approximating the opening in the tissue and an outer circumferential surface, the biasing mechanism including a first biasing mechanism connecting the first ends of both the first curved portion and the second curved portion and a second biasing mechanism connecting the second ends of both the first curved portion and the second curved portion,
wherein the first biasing mechanism and the second biasing mechanism are disposed remotely from each other about the circumference of the annular opening,
wherein the first and second biasing mechanisms exert a force to bias the first curved portion and the second curved portion to the closed position such that the curved annular opening is reduced in size in the closed position,
wherein the biasing mechanism enables the first curved portion and second curved portion to open at least 180 degrees while still approximating the opening in the tissue;
wherein the open position facilitates the biasing mechanism engaging the tissue proximate the opening and the closed position facilitates bringing edges of the tissue opening together to a proximity that allows closure of the opening by a clip or sutures.

14. The tissue support device of claim 13, wherein the first central region and the second central region are have a concave shape.

15. The tissue support device of claim 13, wherein the first biasing mechanism comprises a first hinge and the second biasing mechanism comprises a second hinge, the first hinge joining the first end of the first curved portion with the first end of the second curved portion and the second hinge joining the second end of the first curved portion with the second end of the second curved portion.

16. The tissue support device of claim 13, wherein the first engagement mechanism includes a first needle that extends from a first surface of the first engagement mechanism, and wherein the second engagement mechanism includes a second needle that extends from one of a second surface of the second engagement mechanism.

17. The tissue support device of claim 16, wherein the first and second needles are configured to engage the tissue proximate the opening in the tissue when the first curved portion and the second curved portion are in an open position, wherein the first curved portion and the second curved portion bring the tissue proximate the opening in the tissue closer together in the closed position.

18. The tissue support device of claim 17, wherein the first and second needles curve inwardly toward the opening in the tissue.

19. The tissue support device of claim 13, wherein the first curved portion and the second curved portion are integrated with the biasing mechanism.

20. The tissue support device as recited in claim 13, wherein the biasing mechanism comprises a plurality of hinges, each hinge including a spring.

21. A system for managing access to an opening in tissue comprising:
   a tissue support device as recited in claim 13; and
   a medical device for insertion through the opening formed by the first curved portion and the second curved portion, the medical device having a shaft with a rectangular cross section and a distal end with a flat head edge,
   wherein an entry position for the medical device includes the flat head edge inserted between the first and second curved portions in the closed position,
   wherein an engaged position includes the shaft positioned with longer sides of the rectangular cross section being transverse to the first and second curved portions so as to promote engagement of the plurality of needles with the tissue proximate the opening, and
   wherein a suture position includes the medical device rotated 90 degrees such that thinner sides of the rectangular cross section are positioned transversely between the first and second curved portions so as to facilitate bringing edges of the tissue opening together such that the opening may be closed by using a clip or sutures.

22. A tissue support device for assisting in closing an opening in tissue, the tissue support device comprising:
   a first portion being an elongated member having a first end and a second end and having a first central region defining a concave shape extending therebetween, the first portion having a plurality of first engagement mechanisms extending laterally from the first portion;
   a second portion being an elongated member having a first end and a second end and having a second central region defining a concave shape and extending therebetween, the second portion having a plurality of second engagement mechanisms extending laterally from the second portion in a direction substantially opposed to the first engagement mechanisms when the first portion and the second portion are in a closed position;
   a biasing mechanism joining the first end of the first portion with the first end of the second portion with a first hinge and joining the second end of the first portion with the second end of the second portion with a second hinge such that the first portion and the second portion have an open position where the first portion and the second portion form a closed, clamshell opening approximating the opening in the tissue and an outer circumferential surface, wherein the first hinge and the second hinge are disposed remotely from each other about the circumference of the annular opening, wherein the first hinge and the second hinge of the biasing mechanism exerts a force to bias the first portion and the second portion to the closed position such that the annular opening is reduced in size in the closed position
   wherein the open position facilitates the biasing mechanism engaging the tissue proximate the opening and the closed position facilitates bringing edges of the tissue opening together to a proximity that allows closure of the opening by a clip or sutures.

* * * * *